(12) United States Patent
Sung

(10) Patent No.: US 11,844,960 B2
(45) Date of Patent: Dec. 19, 2023

(54) METHOD FOR EVALUATING RADIOTHERAPY PLANNING

(71) Applicant: GIL MEDICAL CENTER, Incheon (KR)

(72) Inventor: KiHoon Sung, Incheon (KR)

(73) Assignee: GIL MEDICAL CENTER, Incheon (KR)

( * ) Notice: Subject to any disclaimer, the term of this patent is extended or adjusted under 35 U.S.C. 154(b) by 1169 days.

(21) Appl. No.: 16/483,743

(22) PCT Filed: Feb. 6, 2018

(86) PCT No.: PCT/KR2018/001569
§ 371 (c)(1),
(2) Date: Apr. 7, 2020

(87) PCT Pub. No.: WO2018/143767
PCT Pub. Date: Aug. 9, 2018

(65) Prior Publication Data
US 2023/0181929 A1  Jun. 15, 2023

(30) Foreign Application Priority Data
Feb. 6, 2017 (KR) .................. 10-2017-0016108

(51) Int. Cl.
*A61N 5/10* (2006.01)
*G16H 50/30* (2018.01)

(52) U.S. Cl.
CPC .................. *A61N 5/1031* (2013.01)

(58) Field of Classification Search
CPC ....... A61N 5/1031; A61N 5/103; G16H 20/40
See application file for complete search history.

(56) References Cited

U.S. PATENT DOCUMENTS 10,080,911 B2 * 9/2018 Zankowski .......... A61N 5/1031

FOREIGN PATENT DOCUMENTS

| JP | 03-258271 | 11/1991 |
| JP | 2008-178619 | 8/2008 |
| JP | 2016-512778 | 5/2016 |

OTHER PUBLICATIONS

Paddick et al., "A simple dose gradient measurement tool to complement the conformity index,", J Neurosurg (Suppl) 105. 194-201, 2006. (Year: 2006).*

(Continued)

*Primary Examiner* — Christine H Matthews
*Assistant Examiner* — Joshua Daryl D Lannu
(74) *Attorney, Agent, or Firm* — Seed IP Law Group LLP (57) ABSTRACT

The present invention relates to a method for evaluating radiotherapy planning. The present invention provides a method for evaluating radiotherapy planning, the method comprising the steps of: (a) acquiring a dose distribution of generated radiotherapy planning for the target volume according to the prescribed dose; (b) calculating dose gradient index (DGI) of 3-dimensional isodose levels of the acquired dose distribution, by using distances between the isodose levels; and (c) generating a differential dose gradient curve (dDGC) by plotting the calculated dose gradient index (DGI) as a function of the dose over the range of dose distributions.

4 Claims, 7 Drawing Sheets

(56) References Cited

OTHER PUBLICATIONS

Park et al., "New conformity indices based on the calculation of distances between the target volume and the volume of reference isodose," Br J Radiol 2014;87:20140342, 13 pages. (Year: 2014).*

Paddick et al., "A simple dose gradient measurement tool to complement the conformity index,", *J Neurosurg (Suppl)* 105: 194-201, 2006.

Park et al., "New conformity indices based on the calculation of distances between the target volume and the volume of reference isodose," *Br J Radiol 2014*;87:20140342, 13 pages.

\* cited by examiner

| Dose (%) | Dose (Gy) | Surface area (mm²) | Volume (mm³) | dDGI (mm) | cDGI (mm) |
|---|---|---|---|---|---|
| 24 | 3.60 | 16497.6 | 165740.9 | 0.99 | 17.26 |
| 25 | 3.75 | 15268.0 | 150037.0 | 0.87 | 16.27 |
| 26 | 3.90 | 14272.0 | 137215.8 | 0.78 | 15.40 |
| 27 | 4.05 | 13438.1 | 126401.9 | 0.73 | 14.62 |
| 28 | 4.20 | 12682.9 | 116848.6 | 0.65 | 13.89 |
| 29 | 4.35 | 12016.5 | 108844.4 | 0.58 | 13.24 |
| 30 | 4.50 | 11416.7 | 102008.5 | 0.57 | 12.66 |
| ~ | ~ | ~ | ~ | ~ | ~ |
| 50 | 7.50 | 6187.0 | 44735.6 | 0.18 | 5.98 |
| ~ | ~ | ~ | ~ | ~ | ~ |
| 90 | 13.50 | 3722.9 | 21025.7 | 0.10 | 1.13 |
| 91 | 13.65 | 3677.5 | 20655.6 | 0.11 | 1.03 |
| 92 | 13.80 | 3628.4 | 20248.4 | 0.10 | 0.92 |
| 93 | 13.95 | 3586.0 | 19887.5 | 0.11 | 0.82 |
| 94 | 14.10 | 3537.9 | 19486.2 | 0.11 | 0.71 |
| 95 | 14.25 | 3490.1 | 19088.6 | 0.10 | 0.60 |
| 96 | 14.40 | 3444.6 | 18728.2 | 0.11 | 0.50 |
| 97 | 14.55 | 3397.9 | 18335.1 | 0.11 | 0.39 |
| 98 | 14.70 | 3346.7 | 17949.4 | 0.13 | 0.28 |
| 99 | 14.85 | 3293.4 | 17515.5 | 0.15 | 0.15 |
| 100 | 15.00 | 3235.7 | 17035.3 | 0.13 | 0.00 |
| 101 | 15.15 | 3180.6 | 16606.7 | 0.15 | |
| 102 | 15.30 | 3124.0 | 16144.7 | 0.13 | |
| 103 | 15.45 | 3068.3 | 15731.0 | 0.15 | |
| 104 | 15.60 | 3009.2 | 15284.3 | 0.16 | |
| 105 | 15.75 | 2944.0 | 14801.0 | 0.18 | |
| 106 | 15.90 | 2876.2 | 14290.8 | 0.20 | |
| 107 | 16.05 | 2804.1 | 13719.9 | 0.18 | |
| 108 | 16.20 | 2732.5 | 13226.9 | 0.23 | |
| 109 | 16.35 | 2648.1 | 12608.6 | 0.25 | |

[FIG. 8]

| Dose (%) | Dose (Gy) | Surface area (mm²) | Volume (mm³) | dDGI (mm) | cDGI (mm) |
|---|---|---|---|---|---|
| 110 | 16.50 | 2556.7 | 11946.2 | 0.25 | |
| 111 | 16.65 | 2464.2 | 11308.0 | 0.31 | |
| 112 | 16.80 | 2356.9 | 10557.6 | 0.33 | |
| 113 | 16.95 | 2241.2 | 9804.0 | 0.39 | |
| 114 | 17.10 | 2109.2 | 8944.8 | 0.46 | |
| 115 | 17.25 | 1960.4 | 8065.2 | 0.54 | |
| 116 | 17.40 | 1792.9 | 6993.9 | 0.68 | |
| 117 | 17.55 | 1594.9 | 5837.9 | 0.83 | |
| 118 | 17.70 | 1365.5 | 4612.7 | 1.15 | |
| 119 | 17.85 | 1077.1 | 3207.2 | 1.60 | |
| 120 | 18.00 | 731.1 | 1763.2 | 2.29 | |
| 121 | 18.15 | 341.0 | 536.3 | | |

| Plot option | Value | Default value |
|---|---|---|
| Graph type | Differential or Cumulative | |
| Dose | Relative (%) or Absolute (Gy) | |
| Step size | Number (% or Gy) | |
| Scale | | |
| Dose (minimum) | Number (% or Gy) | 0% or 0 Gy |
| Dose (maximum) | Number (% or Gy) | |
| DGI (minimum) | Number (mm) | 0 mm |
| DGI (maximum) | Number (mm) | |
| cDGC origin | Isodose level or PTV | Isodose level |
| cDGC origin isodose | Number (% or Gy) | 100% or Prescription dose |

METHOD FOR EVALUATING RADIOTHERAPY PLANNING

TECHNICAL FIELD

The present invention relates to a method for evaluating radiotherapy planning, and proposes the dose gradient curve (DGC) as a distance-based dose gradient evaluation tool which is independent of target volume.

BACKGROUND ART

Stereotactic radiotherapy, often referred to as stereotactic radiosurgery (SRS) or stereotactic ablative radiotherapy (SABR), is a highly focused radiotherapy technique that delivers an intense radiation dose concentrated on a tumor, while limiting the dose to the surrounding normal tissues.

SRS or SABR plans should be evaluated based on the quality of target coverage to maximize the dose to the target, and on the steepness of the dose gradient outside the target volume to minimize the dose to organ-at-risks (OARs).

A dose-volume histogram (DVH) is most commonly used as a plan evaluation tool to achieve these two objectives.

To determine the quality of target coverage, various conformity indices as suggested in non-patent document 1 have been introduced and widely used as complementary tools. However, there have been limited studies evaluating the dose gradient of the dose distribution.

Dose fall-off characteristics near the target volume can be evaluated by visual inspection of two-dimensional isodose distributions, section by section. It is possible to visualize cross sectional dose profile using dosimetry software, but objective measurement of the dose gradient is nearly impossible.

The gradient index (GI), defined as the ratio of the volume of half the prescription isodose to that of the prescription isodose, has been proposed as a simple dose gradient measurement tool.

Although the GI has allowed quantitative analysis of the dose gradient and comparison of competing plans on the basis of these scores, the complexity of the dose profile over the range of dose distribution cannot be taken into account.

Non-patent document 1: Paddick I Lippitz B. A simple dose gradient measurement tool to complement the conformity index. J Neurosurg 2006; 105 Suppl: 194-201.

DISCLOSURE

Technical Problem

Accordingly, the present invention has been derived to solve the problems of the conventional technologies, and provides a new method for evaluating radiotherapy planning as a distance-based dose gradient evaluation tool.

Technical Solution

In order to achieve the objectives, the present invention provides a method for evaluating radiotherapy planning, the method including: (a) acquiring a dose distribution of generated radiotherapy planning for the target volume according to the prescribed dose (S100); (b) calculating dose gradient index (DGI) of 3-dimensional isodose levels of the acquired dose distribution, by using distances between the isodose levels (S200); and (c) generating a differential dose gradient curve (dDGC) by plotting the calculated dose gradient index (DGI) as a function of the dose over the range of dose distributions (S300).

The differential dose gradient curve (dDGC) can be generated for various calculation intervals (step sizes). As step size refers to the interval between isodose levels used in calculating the differential dose gradient curve (dDGC), the average distance increases with increasing step size. The differential dose gradient curve (dDGC) could be normalized by dividing it by step size, and the normalized differential dose gradient curve (dDGC) provided an adjusted value in a common scale.

The present invention also provides method for evaluating radiotherapy planning, the method including: (a) acquiring a dose distribution of generated radiotherapy planning for the target volume according to the prescribed dose (S100); (b) calculating dose gradient index (DGI) of 3-dimensional isodose levels of the acquired dose distribution, by using distances between the isodose levels (S200); and (c) generating a cumulative dose gradient curve (cDGC) by plotting the cumulative DGI as a function of the dose over the range of dose distributions, wherein the cumulative DGI can be calculated by summing the DGI values from the reference dose to the desired dose (S300').

It may be preferable that (c) includes: plotting a cumulative dose gradient curve (cDGC) together with a dose volume histogram (DVH) in a single plot with double y-axis.

Advantageous Effects

According to the method for evaluating radiotherapy planning according to the present invention can objectively compare various competing treatment plans with respect to the steepness of a dose distribution outside the target volume.

Further, the present invention is a rational method for visualizing the gradient of a dose distribution when the quality of a treatment plan is evaluated, and provides useful information that cannot be obtained by any other indices or display tools.

Accordingly, it can be utilized very usefully in objectively evaluating the gradient of a dose distribution in clinics.

Further, by combining the dose gradient curve (DGC) with the dose-volume histogram (DVH) in a single plot, the dose gradient curve (DGC) can be utilized to evaluate not only the dose gradient but also the target coverage in routine clinical practice.

DESCRIPTION OF THE INVENTION

FIG. 5 illustrates an effect of calculation intervals (step sizes), in which

FIG. 6 illustrates the cumulative dose gradient curve (cDGC) combined with a dose-volume histogram (DVH), in which FIG. 6A illustrates differences in dose gradient (cDGC) and target coverage (DVH) when doses are prescribed (Rx) at 70%, 80%, 85%, and 90% isodose levels in stereotactic radiosurgery (SRS) plans for a virtual target of 3 cm in diameter, and FIG. 6B illustrates an effect of stereotactic radiosurgery (SRS) planning produced for a virtual target having a diameter of 1 cm, and a ring structure of a width of 5 mm around the target represents a dose distribution around a planning target volume (PTV).

BEST MODE

The objectives, features, and other advantages of the present invention will be more apparent by describing exemplary embodiments of the present invention in detail with reference to the accompanying drawings. In addition, terms used herein are defined by taking functions of the present invention into account and can be changed according to user or operator custom or intention. Therefore, definition of the terms should be made according to the overall disclosure set forth herein.

Further, the embodiments are provided exemplarily for description of the present invention, and are not intended to limit the technical scope of the present invention.

Hereinafter, a method for evaluating radiotherapy planning according to an embodiment of the present invention will be described, and to achieve this, indexes and concepts used for the method for evaluating radiotherapy planning will be described first.

1. Dose Gradient Index (DGI)

A dose gradient index is used to measure an average distance between two isodose surfaces.

An isodose surface is defined as the uniform dose contour receiving a certain dose.

The volume and surface area of each isodose level are used to estimate the average distance between two isodose surfaces The isodose surfaces never intersect each other, and the isodose volume of the lower dose level is always larger than that of the higher dose level.

Therefore, an estimation can be made by a simple equation, and the dose gradient index (DGI) can be defined as in Equation 1.

$$DGI = \frac{V_L - V_H}{\frac{1}{2}(S_L + S_H)} \quad \text{[Equation 1]}$$

Figure 1A:
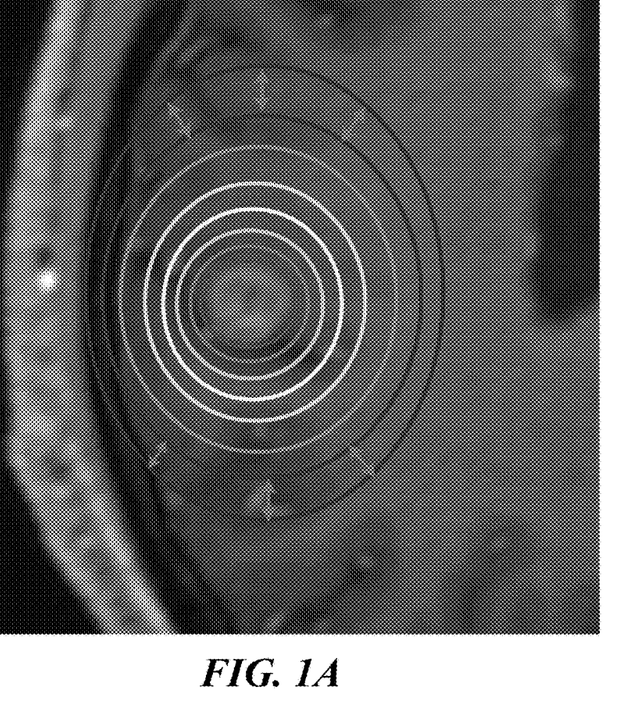
FIG. 1A illustrates a two-dimensional dose distribution displayed using isodose lines on an axial CT-slice.
Figure 1B:
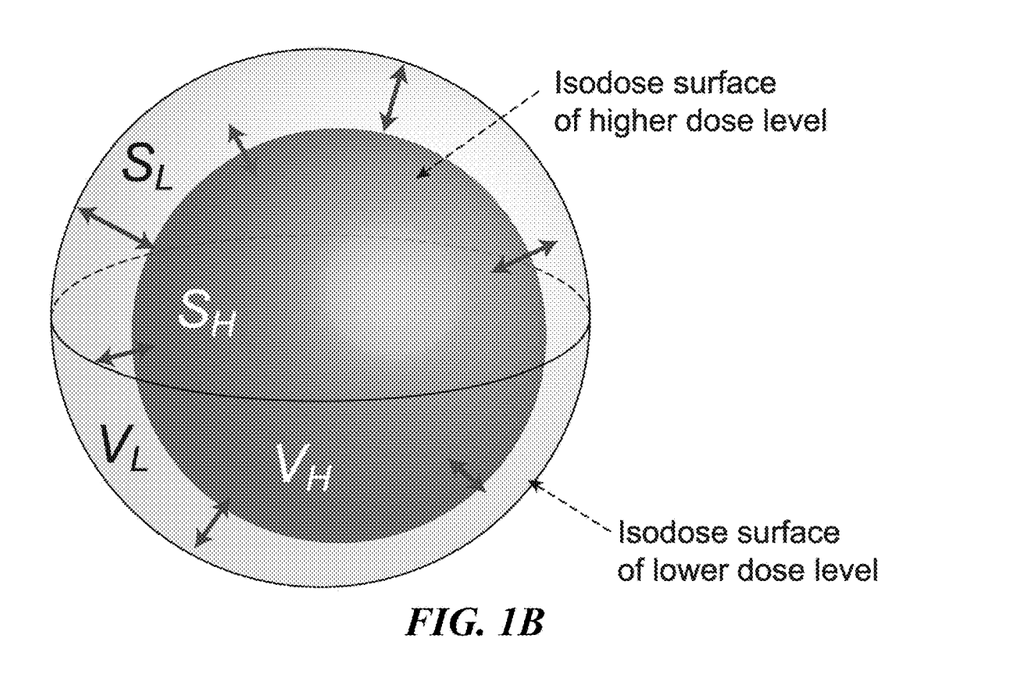
FIG. 1B is a three-dimensional illustration of two isodose surfaces. Double-headed arrows indicate the distances between two isodose surfaces.

In Equation 1, V and S represent the volume and surface area of an isodose level, and the subscripts L and H represent the lower and higher doses, respectively (see FIG. 1B).

In the embodiment, the calculation of the surface areas was made on the basis of a known mesh generation algorithm.

All geometrical analyses were performed by R Statistical Software (version 3.3.2, R for Statistical Computing, Vienna, Austria).

In an R programming environment, the R geometry package (http://geometry.r-forge.r-project.org/) provides high-quality mesh generation and surface triangulation.

Using three-dimensional data points representing the isodose surface, the volume of the isodose contour and its surface area were calculated.

2. Dose Gradient Curve (DGC)

A dose gradient curve (DGC) is a function of doses over the entire dose distribution range and may be defined as a plot of the dose gradient index (DGI), and may be used in two types of differential and cumulative.

2.1 Differential Dose Gradient Curve (dDGC)

A differential dose gradient curve (dDGC) is a plot of dose gradient index of each dose interval as a function of dose.

Figure 7:
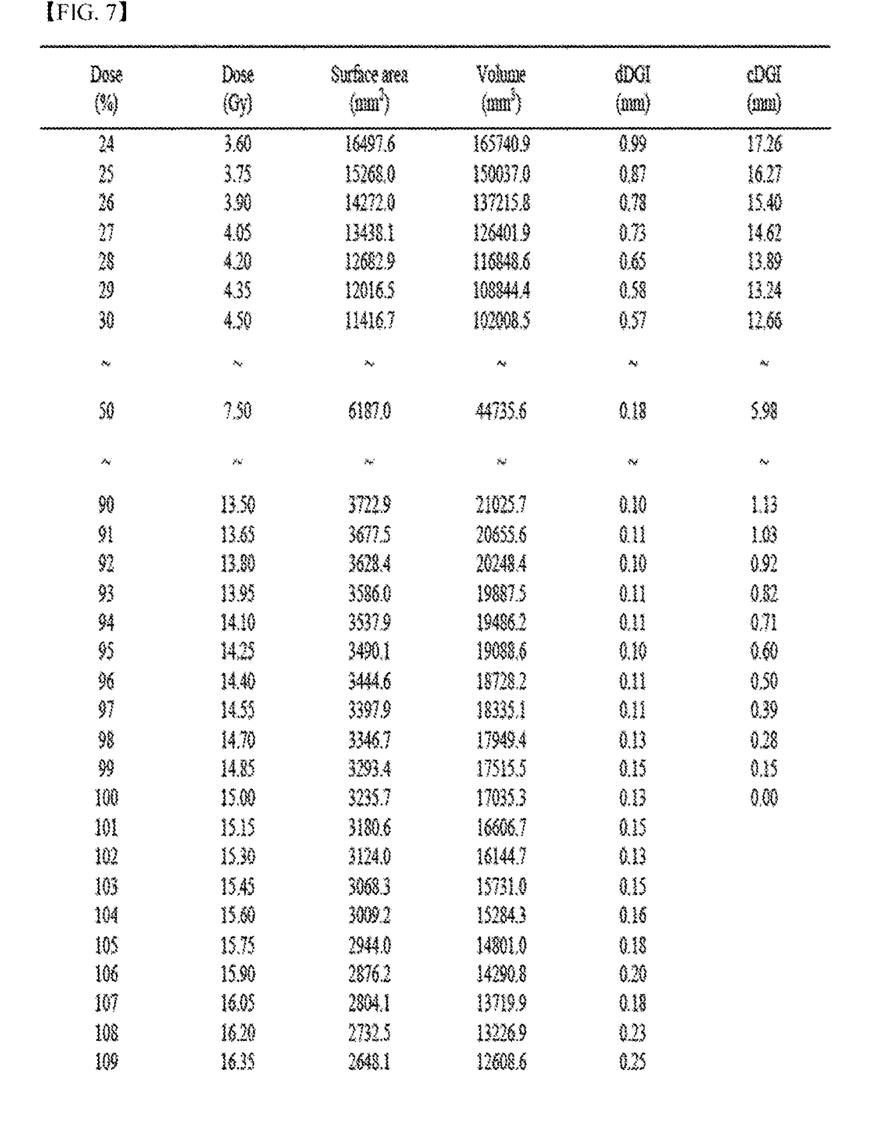
FIGS. 7 and 8 illustrate values appearing according to radiation therapy planning applying verification according to an embodiment of the present invention (the calculation interval is 1%) in stereotactic radiosurgery (SRS) planning, in which a prescribed dose of 15 Gy is applied to a virtual target having a diameter of 3 cm, and the plotted plotting option is illustrated at a lower end of FIG. 8.

From the maximum value of the dose distribution to the dose where the isodose surface intersects the body surface (cropped 3 mm from the skin surface), the dDGC shows the dose gradient of each dose interval by the distance value at a millimeter (mm) scale (see FIG. 7).

2.2 Cumulative Dose Gradient Curve (cDGC)

The cumulative dose gradient curve (cDGC) is a plot of cumulative dose gradient index (cDGI) calculated by summing the DGI values from the reference dose to the desired dose.

The cumulative dose gradient index (cDGI) of the reference dose is set to 0, and then every point plotted in the cDGC indicates the average distance from the reference isodose to each isodose surface (see FIG. 7).

The plotting range of the cDGC is from the reference dose to the dose where the isodose surface intersects the body surface (cropped 3 mm from the skin surface).

Figure 2:
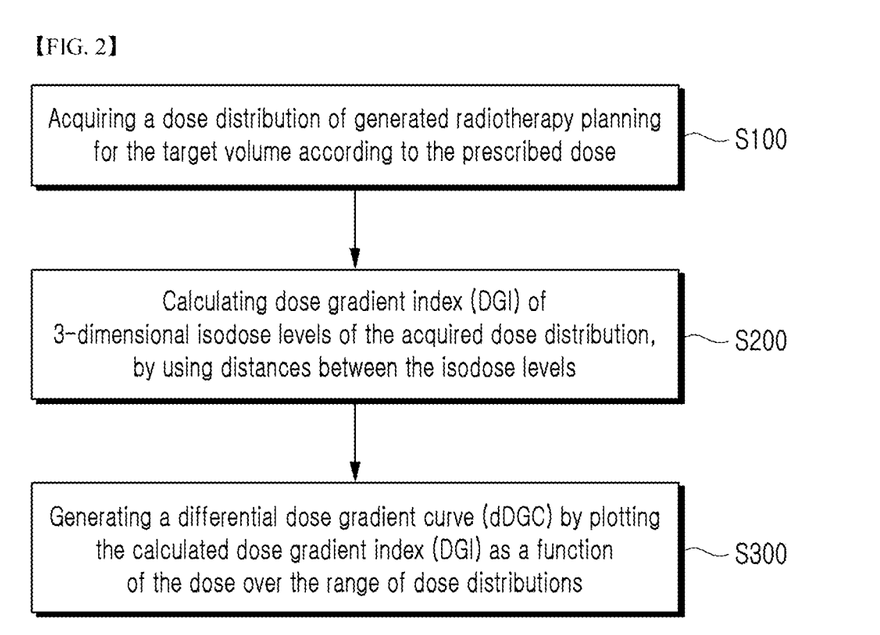
FIGS. 2 and 3 illustrate a method for evaluating radiotherapy planning according to an embodiment of the present invention.
Figure 3:
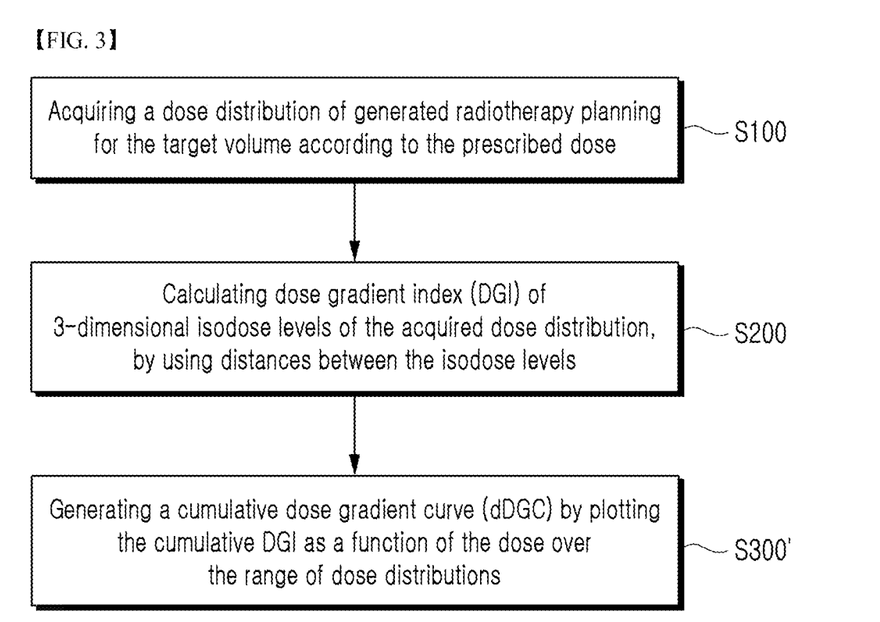

Next, referring further to FIGS. 2 and 7, the method for evaluating radiotherapy planning according to an embodiment of the present invention will be described with a verification example of verifying the method by applying the method to an evaluation of stereotactic radiosurgery (SRS).

First, a dose distribution of a subject target is acquired according to a prescribed dose based on the generated radiotherapy planning (S100).

The performances of the dose gradient curve (DGC) were evaluated with virtual structures as stereotactic radiosurgery (SRS) targets in various planning situations.

Solitary intracranial spherical targets of 1 cm and 3 cm diameter were generated in contouring software.

Single fraction stereotactic radiosurgery (SRS) plans for each virtual target were produced using Dynamic Arc and intensity modulated radiosurgery (IMRS).

The prescription dose was 24 Gy for 1 cm diameter target and 15 Gy for 3 cm diameter target.

Ring structure (5 mm width) around each virtual target was generated to evaluate the dose distribution near the target volume.

Structure delineation and generating SRS plan were performed by the Eclipse treatment planning system (ver. 13.0.33; Varian, Palo Alto, CA, USA). Each isodose level was converted to structure volume. All plans were designed to be delivered on Novalis Tx linear accelerator consisting of high-definition multileaf collimators (HD-MLCs: 2.5 mm leaf width at isocenter).

Three-dimensional coordinate data of all isodose structures were exported to the R environment using the Mirada RTx (version 1.6.2.2, Mirada Medical, Oxford, UK).

Next, dose gradient indexes (DGIs) of isodose levels are calculated by using the average distances of 3-dimensional isodose levels of the acquired dose distribution (S200).

Figure 8:
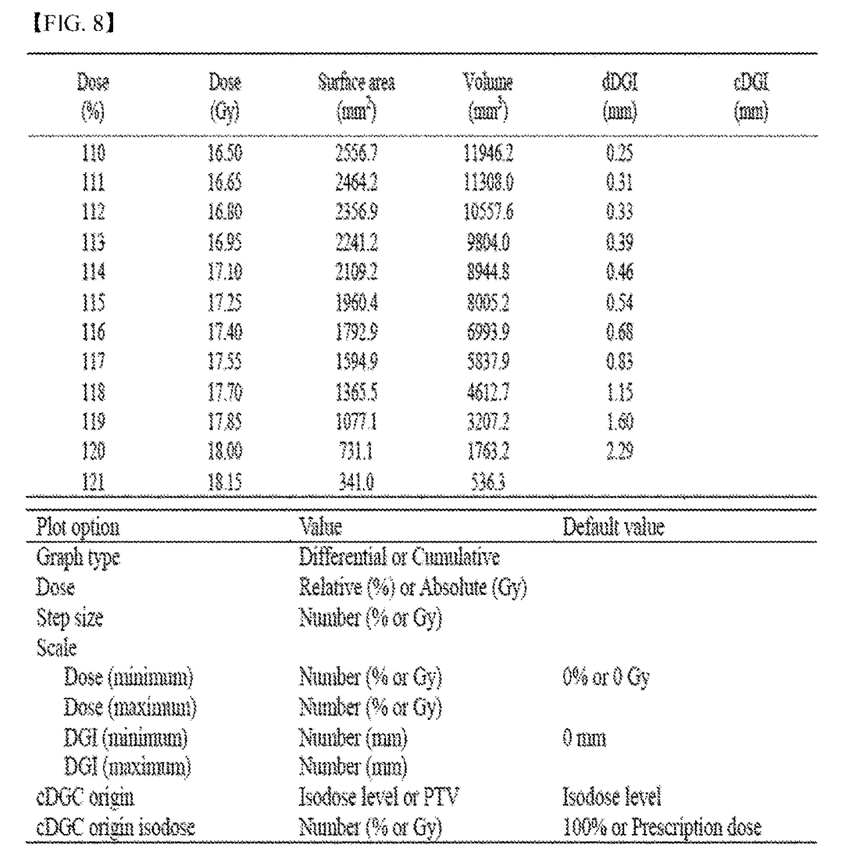

FIGS. 7 and 8 illustrate the results of dose gradient index (DGI) calculation using the SRS plan generated by 3 Dynamic Arc for a virtual target with a 3 cm diameter.

A 15 Gy dose in a single fraction was prescribed, and no normalization was performed.

With a calculation interval (step size) of 1%, the differential dose gradient index (dDGI) ranged from 0.10 to 2.29 mm, and the maximum differential dose gradient index (dDGI) outside the target volume was 0.99 mm.

The cumulative dose gradient index (cDGI) ranged from 0 mm at the reference dose (prescription dose) to 17.26 mm at the 24% isodose level. The cumulative dose gradient index (cDGI) of the 50% isodose level was 5.98 mm.

Next, the calculated dose gradient index (DGI) was plotted in a differential dose gradient curve (dDGC) by using average distance values (S300), and was plotted in a cumulative dose gradient curve (cDGC) by summing the calculated dose gradient index (DGI) from the reference dose (S300').

The data from FIG. 7 were presented by plotting the dose gradient index (DGI) against the dose level, as in the dose gradient curve (DGC).

The dose gradient of each dose interval was plotted as a form of the differential DGC (dDGC) at a millimeter scale (see FIG. 4A).

From the maximum dose to the 24% isodose level, the differential dose gradient curve (dDGC) produced a U-shaped curve.

The minimum value indicating the steepest dose gradient was observed in the range of 70%-90% isodose level.

As shown in FIG. 4B, the cumulative dose gradient curve (cDGC) was generated, and the cumulative dose gradient curve (cDGC) demonstrated a characteristic rotated sigmoid shape when plotted with the cumulative dose gradient index (cDGI) on the y-axis versus the isodose level on the x-axis.

The cumulative dose gradient curve (cDGC) started from the prescription isodose level (cDGI$_{100\%}$=0) and moved downward from there.

Figure 5A:
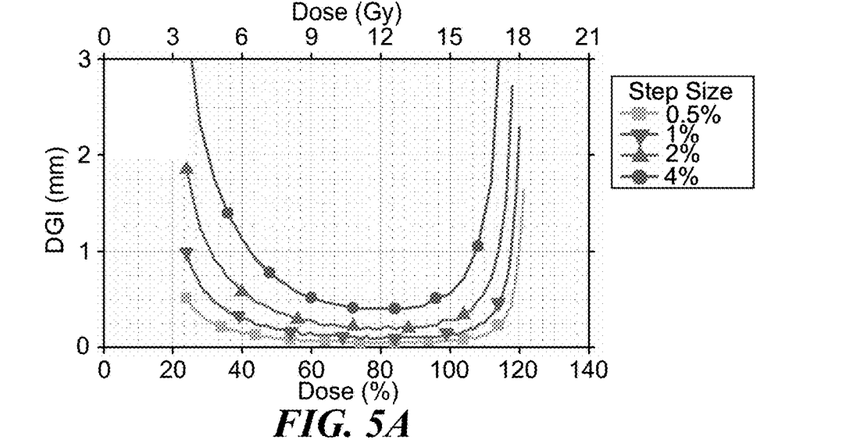
FIG. 5A illustrates the differential dose gradient curve (dDGC) for varying step sizes ranging from 0.5% to 4%.

A differential dose gradient curves (dDGC) for various calculation intervals (step size) were plotted (see FIG. 5A). The differential dose gradient curve (dDGC) increased with increasing step size.

Figure 5B:
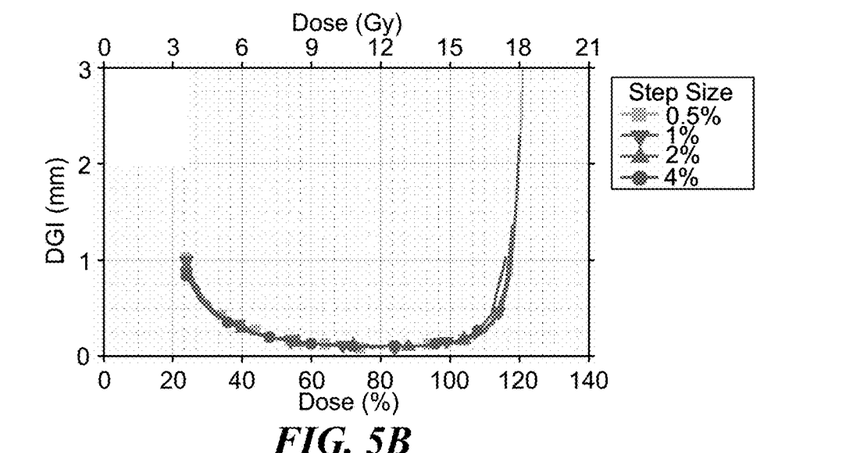
FIG. 5B illustrates the normalized dDGC showing identical calculation results regardless of the difference in step size.

The differential dose gradient curve (dDGC) was normalized by dividing it by the step size, and the normalized differential dose gradient curve (dDGC) showed nearly identical calculation results regardless of the difference in step size (see FIG. 5B).

Figure 5C:
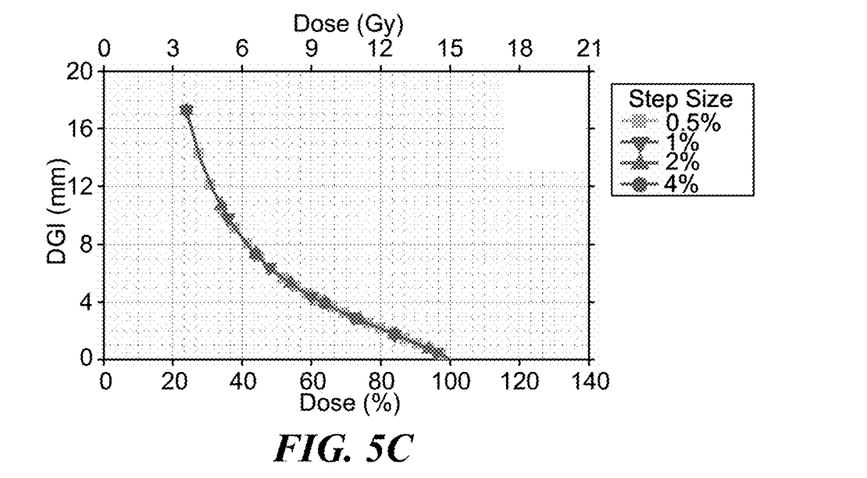
FIG. 5C illustrates the cumulative dose gradient curve (cDGC) for different step sizes, and the cDGC is invariant with respect to changes in step size.

On the other hand, step size had no effect on the calculation results of the cumulative dose gradient curve (cDGC) (see FIG. 5C).

In step S300', the cumulative dose gradient curve (cDGC) may be plotted in a single plot together with an existing dose volume histogram (DVH).

Figure 6:
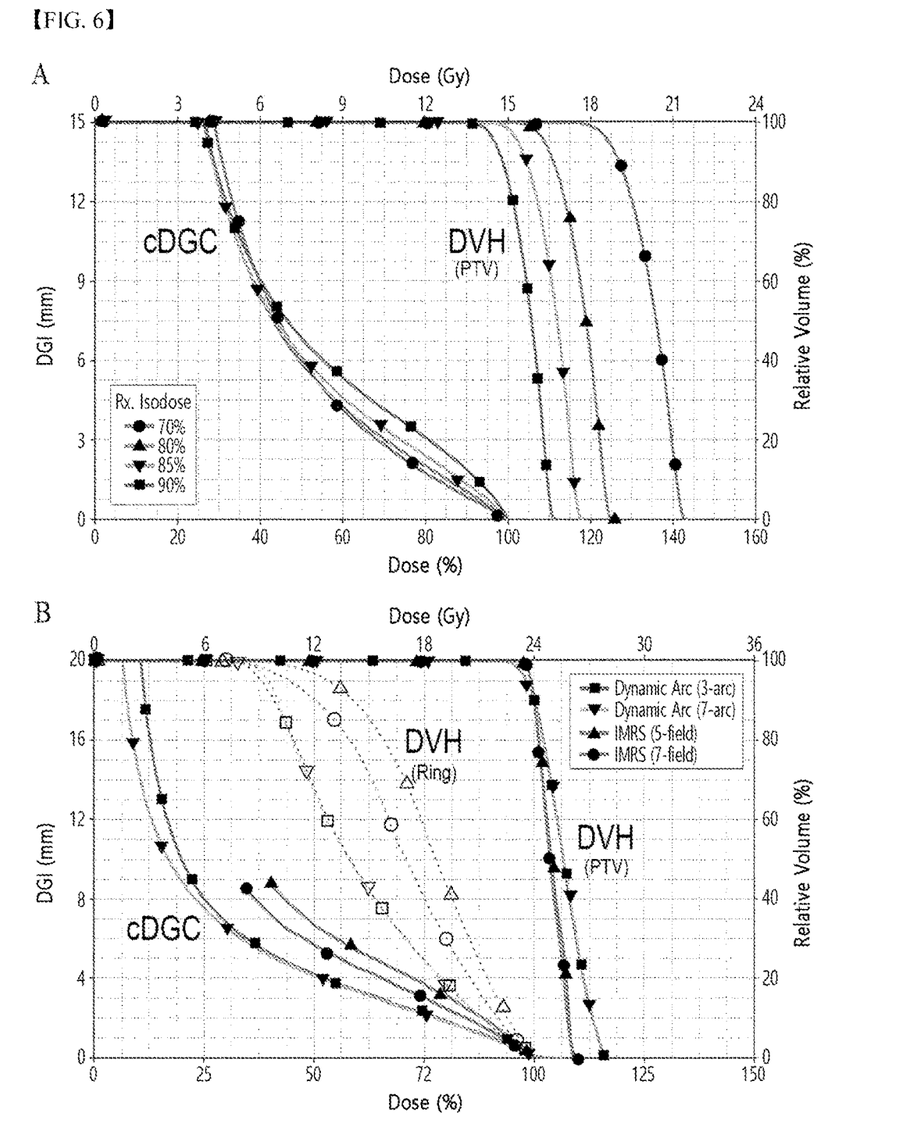

FIG. 6 illustrates a cumulative dose gradient curve (cDGC) plot of a stereotactic radiosurgery (SRS) planning combined with a dose volume histogram (DVH).

The stereotactic radiosurgery planning of FIG. 7 was normalized to prescribe doses to 70%, 80%, 85%, and 90% isodose levels.

As illustrated in FIG. 6A, the cumulative dose gradient curve (cDGC) changed with the prescription (Rx) isodose levels not only in its values but also in its shape.

A strongly concave shape near the prescription dose and the higher levels of the cumulative dose gradient index (cDGI) were observed when a dose of 15 Gy was prescribed to the 90% isodose surface.

The shape of the cumulative gradient curve (cDGC) was gradually changed to a convex shape with a decrease in the prescription isodose, and the lowest level of cumulative gradient curve (cDGC) near the prescription dose was observed with a prescription isodose of 70%.

The Stereotactic radiosurgery (SRS) plans for a virtual target of 1 cm diameter were generated using Dynamic Arc (3- and 7-arc) and intensity modulated radiosurgery (IMRS) (5-field and 7-field), and all plans were normalized to deliver the prescription dose (24 Gy) to at least 90% of the PTV (D$_{90\%}$=100%).

The combined plot demonstrated the influence of varying SRS techniques in the cumulative dose gradient curve (cDGC) and the dose volume histogram (DVH) (see FIG. 6B).

The cumulative dose gradient curves (cDGC) of Dynamic Arc plans showed lower levels than those of intensity modulated radiosurgery (IMRS) plans over the range of plot data examined.

Figure 4:
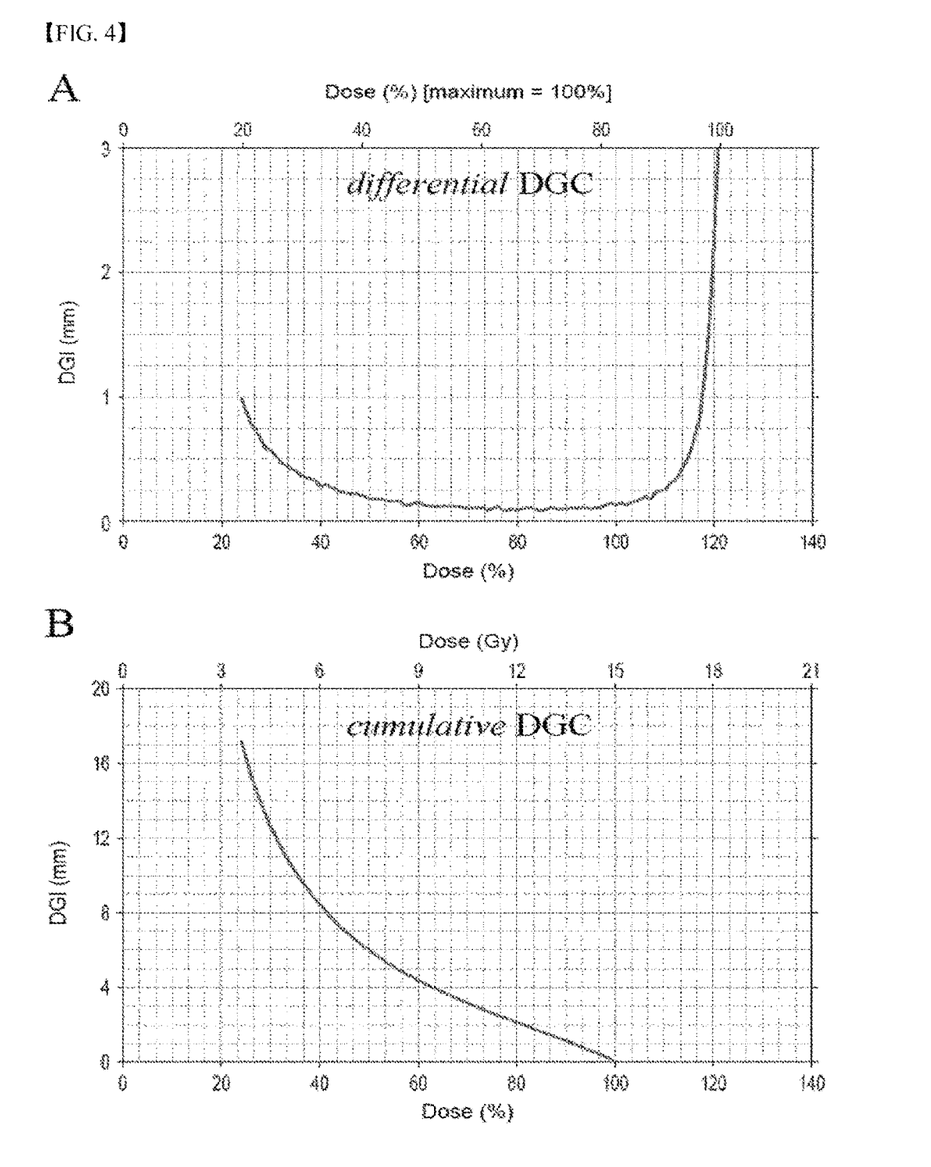
FIG. 4A illustrates a plotted differential dose gradient curve (dDGC) in verification of a new method for evaluating radiotherapy planning according to an embodiment of the present invention, and the plotted points represent average distances of isodose intervals.
FIG. 4B illustrates a plotted cumulative dose gradient curve (cDGC), and the plotted points represent average distances from the surface of the prescribed dose to isodose surfaces.

As illustrated in FIG. 4, the dose gradient curve (DGC) is a rational visualization method for evaluating the plan with respect to the steepness of dose profile.

The dose gradient is represented in an easily understandable format by converting three-dimensional dose distribution to two-dimensional distance between two isodose surfaces.

The differential dose gradient curve (dDGC) provides the dose gradient characteristics over the range of dose distribution regardless of target volume (see FIG. 4A).

In comparison, the cumulative dose gradient curve (cDGC) demonstrates the fall-off characteristics of outside the prescription dose (see FIG. 4B).

As in FIG. 6, the cumulative dose gradient curve (cDGC) was originated from the reference dose level with a value of zero (cDGI$_{reference}$=0) in such a way that the cumulative dose gradient curve (cDGC) could be plotted in a more easily comparable format.

The differential dose gradient curve (dDGC) and cumulative dose gradient curve (cDGC) were equally effective in evaluating the dose gradient, but the differential dose gradient curve (dDGC) was superior for profiling the dose distribution, whereas the cumulative dose gradient curve (cDGC) was superior for comparing rival plans.

The dose gradient curve (DGC) can be generated for various calculation intervals (step sizes).

As step size refers to the interval between isodose levels used in calculating the differential dose gradient curve (dDGC), the average distance increases with increasing step size (see FIG. 5A).

The differential dose gradient curve (dDGC) could be normalized by dividing it by step size, and the normalized differential dose gradient curve (dDGC) provided an adjusted value in a common scale (see FIG. 5B). Meanwhile, no normalization is needed for the cumulative dose gradient curve (cDGC) (see FIG. 5C).

The stereotactic radiosurgery (SRS) or stereotactic ablative radiotherapy (SABR) dose should be prescribed to between the 50% and the 90% isodose level of total dose (not the prescription dose), and a 50% higher dose to the isocenter is acceptable.

The dose gradient outside the target volume should be optimized to achieve the fall-off recommendations.

The two types of dose gradient curves (dDGC, cDGC) can provide useful information in determining the optimal prescription isodose.

For example, it is possible to profile the dose distribution by the differential dose gradient curve (dDGC) such that the data from FIG. 7 revealed the steepest dose gradient in the range of 70%-90% isodose level.

For those range of isodose levels, the cumulative dose gradient curve (cDGC) and the dose volume histogram (DVH) were plotted in a single graph (see FIG. 6).

When a dose of 15 Gy prescribed to the 70% isodose surfaces, the lowest level of the cumulative dose gradient curve (cDGC) was observed, demonstrating the steepest dose gradient near the prescription dose. However, the inversion of the cumulative dose gradient curve (cDGC) was observed around the 40% isodose level.

In contrast, when a dose prescribed to the 90% isodose, the highest level of the cumulative dose gradient curve (cDGC) was plotted, and the dose volume histogram (DVH) revealed insufficient planning target volume (PTV) coverage.

Consequently, the 80% isodose level can be determined as an optimal prescription isodose level.

The Gradient Index (GI) and the Conformity Gradient Index (CGI) have been used for evaluating the dose fall-off outside the prescription isodose volume However, these indices were based on the limited information from two isodose levels (50% and 100%), and cannot reflect all the aspect of the dose distribution, even in the range between 50% and 100% isodose levels. For example, even when the cumulative dose gradient index of 50% (cDGI50%) is the same, the actual dose gradient outside the prescription isodose volume can vary as shown in FIG. 6A.

The choice of the best plan with respect to the dose fall-off should therefore be based on the use of the dose gradient curve (DGC).

The cumulative dose gradient curve (cDGC) provides a chance to quantitatively analyze the steepness of dose gradient, and a method to visually compare competing dose distributions.

By virtue of the combined plot of the cumulative dose gradient curve (cDGC) and the dose volume histogram (DVH), dose gradient as well as target coverage can be evaluated in a single plot.

As shown in FIG. 6B, the dose volume histogram (DVH) for planning target volume (PTV) revealed that the intensity modulated radiosurgery (IMRS) plans produced better target coverage and dose conformity than Dynamic Arc plans. However, the dose volume histogram (DVH) for ring structure showed that the Dynamic Arc plans demonstrated better normal brain sparing outside the target volume than the intensity modulated radiosurgery (IMRS) plans.

Furthermore, the cumulative dose gradient curve (cDGC) represented a good correlation with the dose volume histogram (DVH) for ring structure (see FIG. 6B).

Therefore, the cumulative dose gradient curve (cDGC) can be a powerful tool to evaluate dose distribution and the fall-off characteristics near the target volume without any additional structure to be contoured.

Based on the premise that the isodose surfaces never intersect each other, the range of calculating dose gradient curve (DGC) was limited to the level where the isodose surface intersects the body surface.

The left endpoint of the dose gradient curve (DGC) plot indicates the maximum dose where the isodose started to contact the body surface.

As shown in FIG. 6B, the intensity modulated radiosurgery (IMRS) plans showed a shorter plot range of the cumulative dose gradient curve (cDGC) representing early contact to the body surface at higher level of isodose, due to their speculative nature of dose distribution.

The present invention suggests the evaluation method according to the embodiment as a new method of evaluating radiotherapy planning.

The dose gradient curve (DGC) makes it possible to evaluate the dose gradient comprehensively over the range of dose distribution, and to compare rival plans objectively.

However, the dose gradient curve (DGC) does not provide any directional information but provide the average distance between two isodose surfaces.

Despite some drawbacks, our results demonstrate that the dose gradient curve (DGC) provide the useful information that cannot be obtained by any other indices or display tools.

The dose gradient curve (DGC) is a rational method for visualizing the dose gradient in evaluating the plan with respect to the steepness of dose profile.

Moreover, by combining with the dose volume histogram (DVH) in a single plot with the same dose scale, the dose gradient curve (DGC) is utilized to evaluate not only dose gradient but also target coverage in routine clinical practice.

Although the preferred embodiments of the present invention have been described, the present invention is not limited to the above-described specific embodiments. That is, an ordinary person skilled in the art to which the present invention pertains can variously change and correct the present invention without departing from the scope and scope of the claims, and the equivalents of all the changes and modifications will be regarded as pertaining to the scope of the present invention.

The invention claimed is:

1. A method for evaluating radiotherapy planning, the method comprising:
   (a) acquiring a dose distribution of a generated radiotherapy planning for a target volume according to a prescribed dose;
   (b) calculating dose gradient indexes (DGIs) of 3-dimensional isodose levels of the acquired dose distribution, by using distances between the 3-dimensional isodose levels; and
   (c) generating a differential dose gradient curve (dDGC) by plotting the calculated dose gradient indexes (DGIs) as a function of the dose over a range of the acquired dose distributions.

2. The method of claim 1, wherein the dose gradient indexes (DGIs) are generated for multiple calculation intervals, and the differential dose gradient curve (dDGC) is normalized by dividing the differential dose gradient curve by a corresponding calculation interval.

3. A method for evaluating radiotherapy planning, the method comprising:
   (a) acquiring a dose distribution of a generated radiotherapy planning for a target volume according to a prescribed dose;
   (b) calculating dose gradient indexes (DGIs) of 3-dimensional isodose levels of the acquired dose distribution, by using distances between the 3-dimensional isodose levels; and (c) generating a cumulative dose gradient curve (cDGC) by plotting cumulative dose gradient indexes (DGIs) as a function of the dose over a range of the acquired dose distributions, wherein the cumulative dose gradient indexes (DGIs) are calculated by summing the calculated dose gradient indexes (DGIs) of the 3 dimensional isodose levels, and wherein the cumulative dose gradient curve (cDGC) is originated from the prescribed dose having an isodose level of 100%.

4. The method of claim 3, wherein (c) comprises:
plotting the cumulative dose gradient curve (cDGC) together with a dose volume histogram (DVH) in a single plot with double y-axes.

* * * * *